(12) United States Patent
Shoureshi et al.

(10) Patent No.: US 6,382,029 B1
(45) Date of Patent: May 7, 2002

(54) APPARATUS AND METHOD FOR UTILIZING ELECTROMAGNETIC ACOUSTIC TRANSDUCERS TO NON-DESTRUCTIVELY ANALYZE IN-SERVICE CONDUCTIVE MATERIALS

(75) Inventors: Rahmat A. Shoureshi, Golden; Michael T. Chenowith, Westminister; George A. Alers, Boulder, all of CO (US)

(73) Assignees: The United States of America as represented by the Secretary of Commerce; The 14th and Constitution National Institute of Standards and Technology, both of Washington, DC (US); Colorado School of Mines, Golden, CO (US)

( * ) Notice: Subject to any disclaimer, the term of this patent is extended or adjusted under 35 U.S.C. 154(b) by 0 days.

(21) Appl. No.: 09/519,954

(22) Filed: Mar. 7, 2000

(51) Int. Cl.⁷ .......................... G01N 29/04; G01B 5/30; G08B 21/00
(52) U.S. Cl. .............................. 73/643; 73/624; 73/628; 73/633; 702/39; 340/652
(58) Field of Search .................... 73/643, 596, 599, 73/600, 602, 627, 628, 618, 620, 622, 624, 632, 633, 634, 637, 638; 702/35, 34, 36, 39; 340/635, 652

(56) References Cited

U.S. PATENT DOCUMENTS

| | | | | |
|---|---|---|---|---|
| 3,244,975 A | * | 4/1966 | Bauer | 324/523 |
| 3,255,406 A | * | 6/1966 | Schluter | 324/523 |
| 4,104,922 A | * | 8/1978 | Alers et al. | 73/643 |
| 5,530,364 A | * | 6/1996 | Mashikian et al. | 324/529 |

* cited by examiner

Primary Examiner—Richard A. Moller
(74) Attorney, Agent, or Firm—Pennie & Edmonds LLP

(57) ABSTRACT

The method of the invention identifies damage to an in-service conductor associated with the delivery (transmission and distribution) of electric power. Electro-magnetic acoustic energy is generated in an in-service conductor associated with the delivery of electric power. Corresponding return electro-magnetic acoustic energy is then measured. Features are then extracted from the return electro-magnetic acoustic energy to characterize damage to the in-service conductor. The features may be extracted through a variety of signal processing techniques, such as wavelet signal processing. The extracted features may be classified using a neural network, fuzzy logic, or a combination of both.

26 Claims, 6 Drawing Sheets

APPARATUS AND METHOD FOR UTILIZING ELECTROMAGNETIC ACOUSTIC TRANSDUCERS TO NON-DESTRUCTIVELY ANALYZE IN-SERVICE CONDUCTIVE MATERIALS

BRIEF DESCRIPTION OF THE INVENTION

This invention relates generally to the non-destructive analysis of conductive materials, such as conductive materials utilized in electric power transmission and distribution infrastructure. More particularly, this invention relates to a technique of using electro-magnetic acoustic transducers to non-destructively analyze in-service conductive materials.

BACKGROUND OF THE INVENTION

Diagnostic methods are widely used throughout industry. Often times, diagnostic evaluation is performed by life cycle, or stress testing. For instance, automobile manufacturers test the safety of their car designs by crashing cars under conditions that simulate an accident on the road. Manufacturers of bicycle frames test their designs by cycling loads until failure results. This type of testing is not useful in many instances. The expense of this type of destructive testing is too great for products, such as bridges or buildings. Infrastructure, such as power lines or phone lines, also requires testing that does not destroy or introduce service disruption.

The power industry contains an enormous amount of infrastructure. This infrastructure includes a vast network of transmission lines, distribution lines, and supporting equipment. There is an acute need for devices that can easily provide information regarding the integrity of electrical conductivity and mechanical connectivity of electric power transmission and distribution infrastructure, referred to herein as electric power delivery infrastructure. In particular, it is important to assess information, such as: the integrity of ground connections, the degree of oxidation in conductors, corroded or broken strands in conductors, and discontinuity and damage within shoes or marker balls of transmission lines.

Electric power delivery infrastructure is commonly difficult to access. For example, electric power distribution equipment commonly includes a buried ground mat that is connected to the equipment through a riser that extends from the ground mat to the equipment. Present techniques to analyze a riser requires that the riser be dug out from the ground for examination. For overhead power line conductors, the conductor suspension assembly must be disassembled to inspect the conductor within the assembly. Thus, this prior art technique is very tedious, labor intensive, and costly. In almost all cases, the equipment or transmission line cannot be energized during this manual inspection process. In other words, in-service inspection is not possible. Thus, at the present time, it is very costly to assess the integrity of any type of conductor within the electric power delivery infrastructure.

In view of the foregoing, it would be highly desirable to provide an improved technique for analyzing conductors within the electric power delivery infrastructure. Ideally, the technique would be operative on equipment in its installed, in-service state. In other words, the technique would be nondestructive to the conductor being analyzed during normal operation.

SUMMARY OF THE INVENTION

The method of the invention identifies damage to an in-service conductor associated with the delivery (transmission or distribution) of electric power. Electro-magnetic acoustic energy is generated in an in-service conductor associated with the delivery of electric power. Corresponding return electro-magnetic acoustic energy is then measured. Features are then extracted from the return electro-magnetic acoustic energy to characterize damage to the in-service conductor. The features may be extracted through a feature analyzer, such as a wavelet analyzer or other signal analyzer. The extracted features may be classified using a neural network or fuzzy logic.

The apparatus of the invention identifies damage to an in-service conductor associated with the delivery of electric power. The apparatus includes a transmitting electro-magnetic acoustic transducer configured for engagement with the in-service conductor through an electro-magnetic coupling. The transmitting electro-magnetic acoustic transducer applies a transmitted signal to the conductor. A receiving electro-magnetic acoustic transducer configured for engagement with the conductor receives a return signal from the in-service conductor that corresponds to the transmitted signal. A feature extraction module identifies selected attributes of the return signal. The feature extraction module may include such advanced signal processing techniques as a neural network module and/or a fuzzy logic module to facilitate the feature extraction process.

The invention provides a non-destructive probing sensor that can be used with an in-service conductor used to deliver electric power. Thus, the non-destructive probing sensor can be used without disconnecting or excavating conductors.

The transducers of the invention do not require a couplant with the conductor under test. The absence of a couplant eliminates errors caused by couplant variations, and increases the accuracy of the instrumentation. In addition to its electro-magnetic coupling, the sensors of the invention work at high temperatures and pass through various coatings while scanning at high speeds. Because there is no incidence angle or crystal selection required, the transducers of the invention are less prone to operator error and produce more repeatable results.

BRIEF DESCRIPTION OF THE DRAWINGS

For a better understanding of the invention, reference should be made to the following detailed description taken in conjunction with the accompanying drawings, where.

Like reference numerals refer to corresponding parts throughout the drawings.

DETAILED DESCRIPTION OF THE INVENTION

Figure 1:
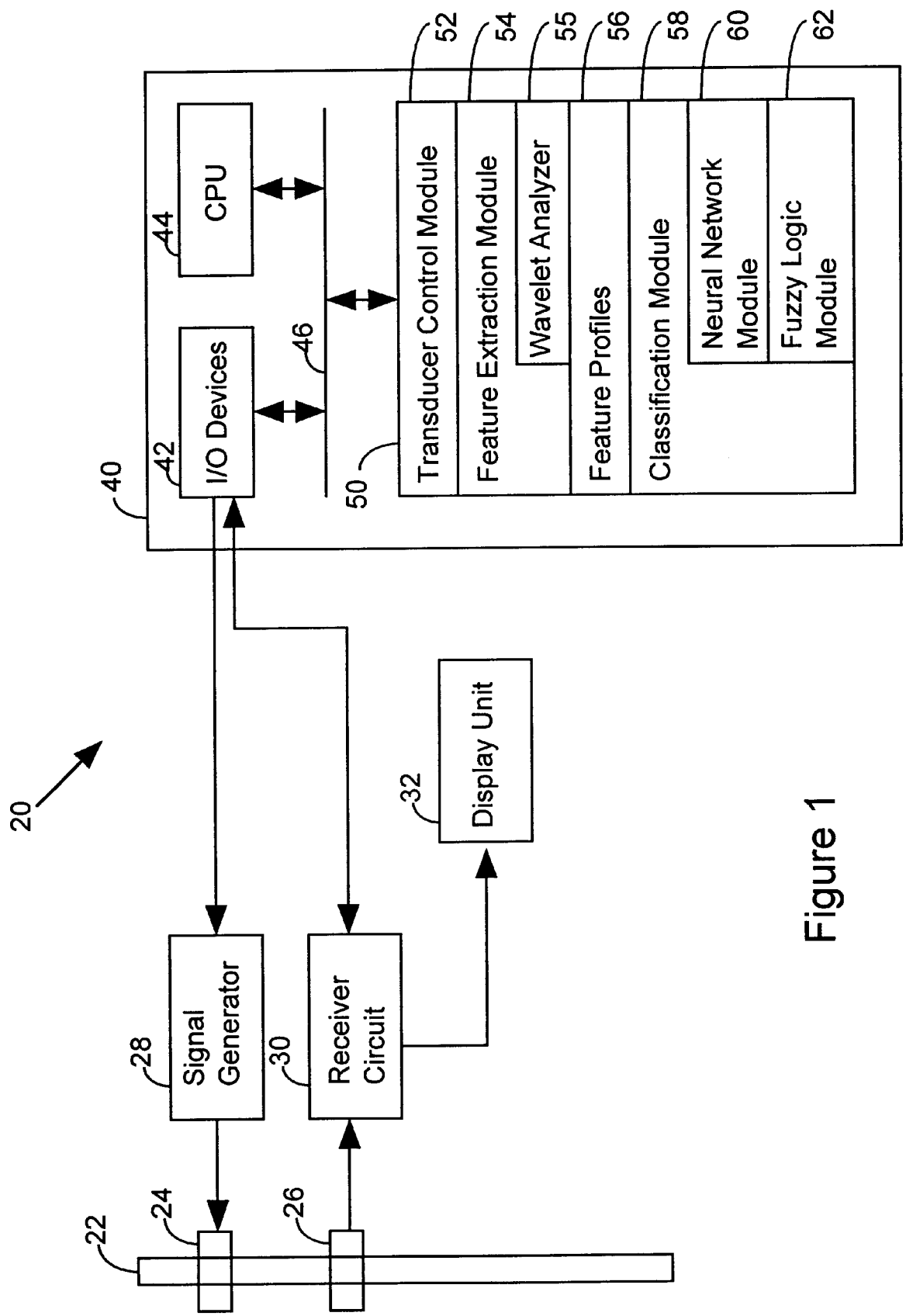
FIG. 1 illustrates an Electro-Magnetic Acoustic Transducer (EMAT) system for non-destructive evaluation of a conductor in accordance with an embodiment of the invention.

FIG. 1 illustrates an Electro-Magnetic Acoustic Transducer (EMAT) based system 20 for the non-destructive evaluation of an in-service conductor associated with the delivery (transmission or distribution) of electric power. In accordance with the invention, the in-service conductor can be analyzed during normal system operation. By way of example, the in-service conductor may be a transmission line, a ground connection, a ground mat riser, a support wire, or a marker ball of a transmission line.

FIG. 1 includes a simplified depiction of an in-service conductor 22. The in-service conductor 22 is analyzed for defects utilizing the disclosed system 20. The disclosed system 20 includes a transmitting electro-magnetic acoustic transducer 24 to apply electro-magnetic acoustic energy to the conductor 22. The system 20 also includes a receiving electro-magnetic acoustic transducer 26 to receive return electro-magnetic acoustic energy from the conductor 22.

A signal generator 28 is used to produce the electromagnetic acoustic energy signal at the transducer 24. Preferably, the signal generator 28 operates under the control of a computer or similar processing unit 40.

A receiver circuit 30 processes the signal from the receiving electro-magnetic acoustic transducer 26. In one embodiment of the invention, the signal from the receiver circuit 30 is applied to a display unit 32, e.g., an oscilliscope. The signal is also applied to the processing unit 40. Preferably, the receiver circuit 30 operates under the control of the computer 40.

The computer 40 includes a set of input/output devices 42. The input/output devices 42 include a connector for communication with the signal generator 28, a connector for communication with the receiver circuit 30, a keyboard, a mouse, a video monitor, a printer, and the like. The input/output devices 42 may also include an oscilliscope. The input/output devices 42 are connected to a central processing unit 42 via a system bus 46. Also connected to the system bus 46 is a memory 50. The architecture of the computer 40 is standard, except that the computer includes a set of executable code to implement functions in accordance with the invention. Those skilled in the art will appreciate that instead of a conventional computer, other types of data processing devices may be used in accordance with the invention.

The memory 50 stores a transducer control module 52. The transducer control module 52 performs standard supervisory and interface operations with the signal generator 28 and receiver circuit 30.

The memory 50 also stores a feature extraction module 54. The feature extraction module 54 extracts features from the signal received at the transducer 26 to identify flaws in the conductor 22. In a preferred embodiment of the invention, the feature extraction module 54 includes a wavelet analyzer 55 to perform a wavelet analysis of the type described below.

The extracted features are then compared to a set of feature profiles 56. Each feature profile 56 characterizes a signal associated with a predetermined fault at a selected location of the conductor 22.

The extracted features are compared to the stored feature profiles 56 to characterize the type and location of a fault in the conductor 22. This comparison may be accomplished with a classification module 58. As discussed below, the classification module 58 may include a neural network module 60 to classify the extracted features with respect to the stored profiles 56. Alternately, the classification module 58 may use a fuzzy logic module 62 to classify the extracted features with respect to the stored profiles 56. Those skilled in the art will recognize that other signature analysis techniques may also be used in accordance with the invention.

Figure 2:
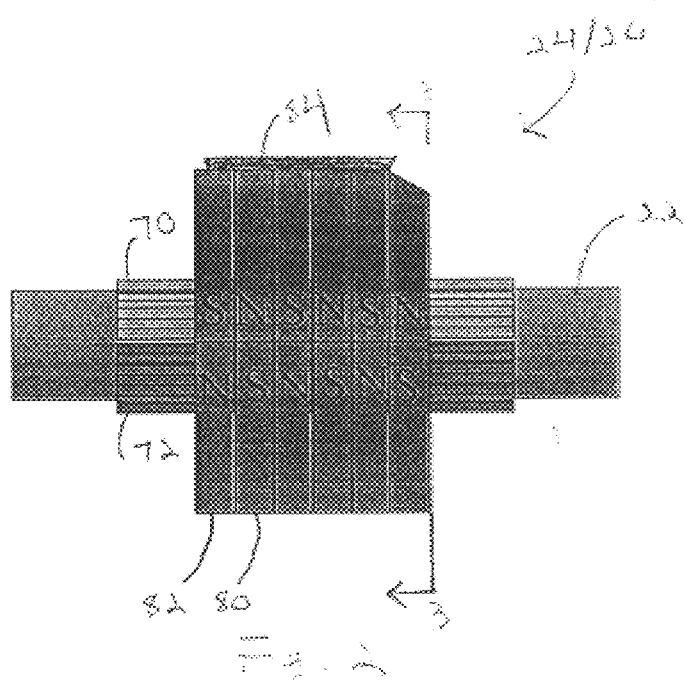
FIG. 2 illustrates an EMAT transducer utilized in accordance with an embodiment of the invention.
Figure 3:
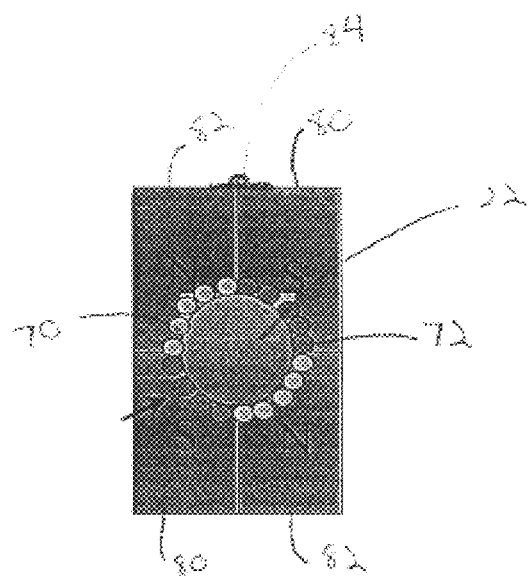
FIG. 3 is a side cross-sectional view of the EMAT transducer taken along the line 3—3 of FIG. 2.
Figure 4:
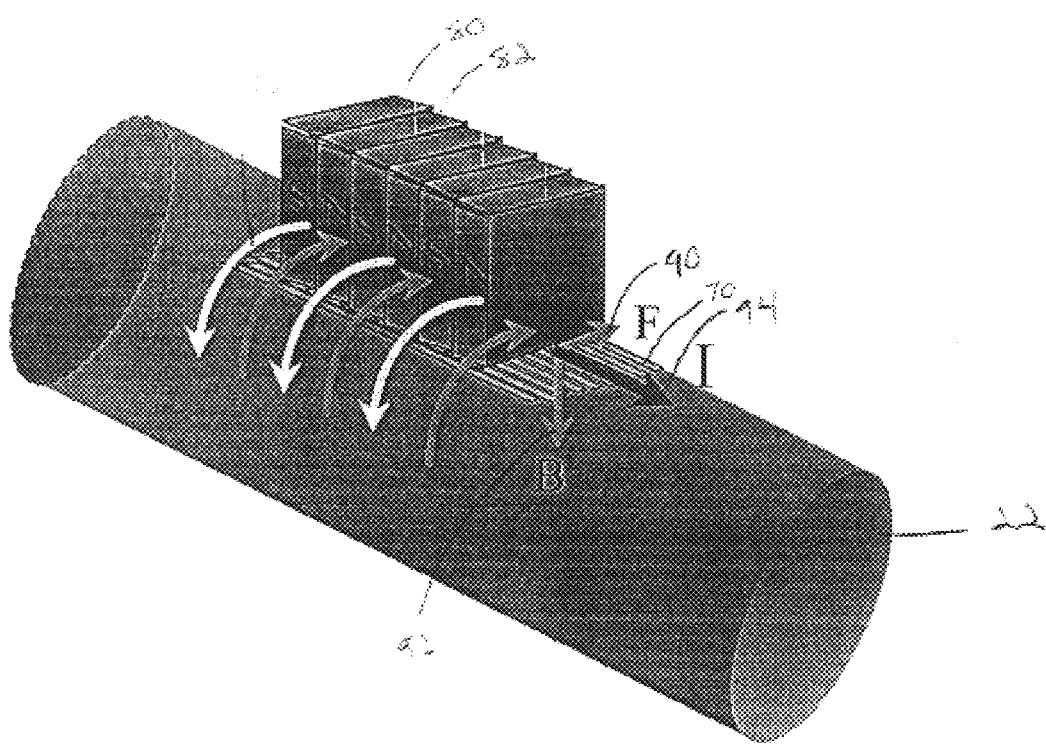
FIG. 4 illustrates forces and torques created in accordance with an EMAT transducer of the invention.

The operation of the system 20 of FIG. 1 is more fully appreciated in reference to FIGS. 2–4 and the following discussion. FIG. 2 illustrates an electro-magnetic acoustic transducer 24 or 26 utilized in accordance with the invention. The transducer includes a set of forward current coils 70 and return current coils 72 surrounded by magnets 80 and 82 of alternating polarity. The transducer 24/26 surrounds a conductor 22. A latch 84 allows the magnets 80/82 to be opened so that the transducer 24/26 can be positioned on the conductor 22.

FIG. 3 is a cross-sectional view taken along the line 3—3 of FIG. 2. FIG. 3 illustrates the magnets 80 and 82 of alternating polarity. The figure also illustrates the forward current coils 70 and the return current coils 72. Further, the figure illustrates the latch 84. As can be appreciated in FIG. 3, by pivoting the magnets on the right-side of the figure at the latch 84, the transducer can be positioned on the conductor 22. Naturally, the invention may be implemented using other arrangements for the magnet, coils, and latch mechanisms.

Electro-magnetic acoustic transducers (EMATs) derive their name from the fact that they can excite and detect ultrasonic vibrations in metals by an electro-magnetic induction process across an air gap. EMAT's overcome many of the common problems encountered with traditional ultrasonic techniques, in addition to having electro-magnetic coupling, EMATs work at high temperatures and pass through various coatings while scanning at high speeds. Because there is no incidence angle or crystal required, EMATs are less prone to operator error and produce a more repeatable variety of ultrasonic wave modes. Numerous modes of acoustic waves can be generated depending on the design of the transducer.

The coil 70 in the transmitting EMAT 24 is placed as close as possible to the conductor 22. The signal generator 28 applies an alternating current, with desired frequency and amplitude, to the coil 70. The alternating current produces a dynamic magnetic field, which varies in time and space. The magnetic field induces an eddy current in the conductor 22. The eddy current follows the path of the coil, but is smaller than the driving current because of the air gap.

To create a force in the metal, the permanent magnets 80 and 82 are placed directly over the coil to flood the conductor 22 with magnetic flux. The eddy current interacts with the external magnetic induction to produce a force density coupled to the lattice of the conductor. This force is called a Lorentz force. The Lorentz force excites the particles of the test specimen, in this case the in-service conductor. The force on the perimeter of the conductor creates a torque effect, as shown in FIG. 4.

FIG. 4 illustrates the various forces and torques that operate on the conductor 22. The figure illustrates a motive force field 90, a magnetic force field 92, and a current force field 94. The figure also illustrates eddy currents 96 formed within the conductor 22. The eddy currents 96 interact with the static magnetic field to produce stresses in the conductor 22 leading to the generation of ultrasonic waves. The frequency of the current, the shape of the EMAT transducer, its position in the magnetic field, and the thickness of the conductor, combine to determine the vibration mode of the conductor which is excited by ultrasonically generated waves. The vibration mode and frequency determine the type of analysis to be performed.

The generated ultrasonic waves are reflected from conductor defects, e.g., a broken conductor strand, oxidation, or a loose connection. The reflected energy produces a current in the coil 72 of the receiver 26. In particular, when the reflected acoustic wave passes under the receiver 26, the surface of the material is displaced in the magnetic field. An electric field arises because of the interaction of the magnetic field and the time varying particle velocity. The time varying particle velocity incorporates reflected and incident elastic waves at the surface. The electric field produces a receiver voltage that is sensed and processed in accordance with the invention. The sensed signal has attributes that characterize any flaws in the conductor 22.

The invention has been successfully implemented with coils 70 and 72 in the shape of a spiral. Coils in this shape generate waves that enter or leave the conductor 22 perpendicular to the surface in a direct analog to the conventional piezoelectric transducer. If a round spiral coil is placed under a single pole piece of a magnet 80 or 82, a shear wave is generated whose polarization is in the radius direction of the spiral; i.e., a circular polarized ultrasonic wave. A rectangular spiral generates a shear wave that is polarized linearly in the direction perpendicular to the long axis of the rectangle. The magnetic field must be configured so that a north pole is over one side on the long-axis centerline and a south pole is on the other side. This is easily accomplished by using two permanent magnets stacked side by side with opposite pole orientation and by placing the magnet-to-magnet boundary on the long-axis centerline.

The efficiency of an EMAT transducer depends on the square of the magnetic field at the metal surface. Hence, the source of magnetic field plays a crucial role in the implementation of an EMAT inspection system. The largest fields are obtained by DC electro-magnets that use iron cores with specially shaped pole pieces to focus the field to the area of the EMAT coil. Fields approaching 2T (20 kilogauss) over areas of a few millimeters on each side can be obtained in this way. Unfortunately, such electro-magnets are bulky (about 0.1 m$^3$) and massive (over 45 kg) so they are usually applicable only for on-line inspections in pipe and bar mills where the material-handling machinery easily dwarfs the electro-magnet and its power supply.

Small, handheld probes similar to the familiar piezoelectric transducer can be constructed out of carefully shaped rare earth permanent magnets, such as samarium-cobalt or neodymium-iron-boron alloys. In these cases, fields in the range of 0.3–0.5 T (3–5 kilgauss) can be applied to coils whose range from a few millimeters on a side to several square centimeters.

An intermediate-size electro-magnet can be constructed with a laminated iron core so that high fields can be obtained for a short time by driving a large pulse of current through the coil. Because the drive current flows can be obtained for only a few milliseconds, the average power dissipated is quite manageable and fields near 1T (10 kilogausss) can be achieved over areas of a few square centimeters. This class of magnet is very appropriate for automatic inspection systems in which the transducer must be lifted on and off the workpiece or mechanically scanned over large areas.

The signal received at the transducer 26 is processed for feature extraction. As previously indicated, a feature extraction module 54 operating on computer 40 may be used for this purpose. The feature extraction module 54 may include a wavelet analyzer 55. The wavelet analyzer 55 includes executable code to perform an automated wavelet analysis of the type discussed below.

The integral wavelet transform is used as a tool for time-frequency analysis. A wavelet may be characterized as:

$$g(t) = e^{\left(\frac{-t^2}{2} + jmt\right)}$$

This wavelet is a complex sinusoid $e^{jmt}$=cos mt+j sin mt scaled by the Gaussian function $$e^{\frac{-t^2}{2}} \equiv Gaussian.$$

The Gaussian distribution is well known as having a small time-bandwidth product. In other words, it is well concentrated in time and frequency. A wavelet that can be used for the EMAT sensor data of the invention is a sinusoid scaled by a normal (or Gaussian) distribution and includes 10 periods of the sinusoid. The design of the wavelet for EMAT data analysis is orthogonal Given a set of functions $\{\phi_n(x)\}$ n=1,2,3 . . . defined over an interval (a,b) which can be finite or infinite, the functions are said to be orthogonal if:

$$\int_a^b \phi_m(x)\phi_n(x)dx \begin{cases} = 0 \longrightarrow m \neq n \\ \neq 0 \longrightarrow m = n \end{cases}$$

Figure 5:
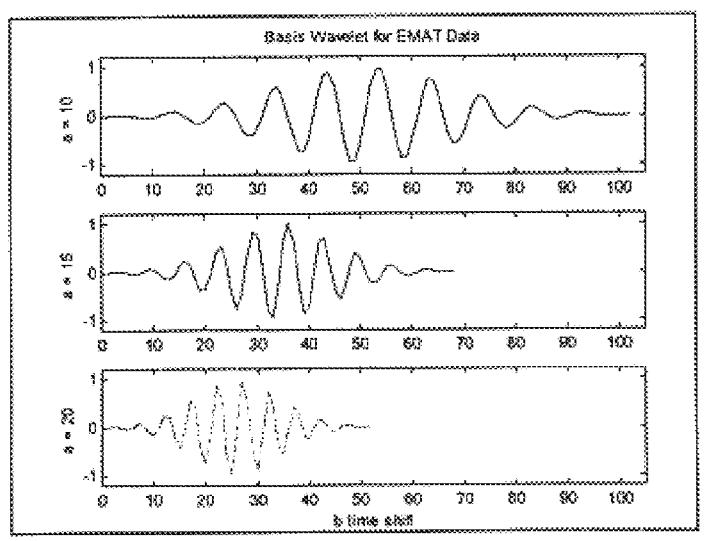
FIG. 5 illustrates a basis wavelet for EMAT data processed in accordance with an embodiment of the invention.

To prove orthogonality, all possible scales of the basis wavelet must sum to zero when multiplied together. In order to get the most information from a wavelet transform pertaining to the data, the basis function should be similar to characteristics of the data (i.e. the wave packets). The possible scales of the wavelet range from 1 to 100 with 1 being the lowest frequency (widest time interval) and 100 being the highest frequency (smallest time interval). FIG. 5 shows several scales of the wavelet basis function used in accordance with an embodiment of the invention.

Orthogonality of the wavelet basis function is proven by multiplying all scales of the wavelet together, which include 1 to 100. In one embodiment, this results in a sum of the product of the wavelets over time equal to −8.9713e-106.

Figure 6:
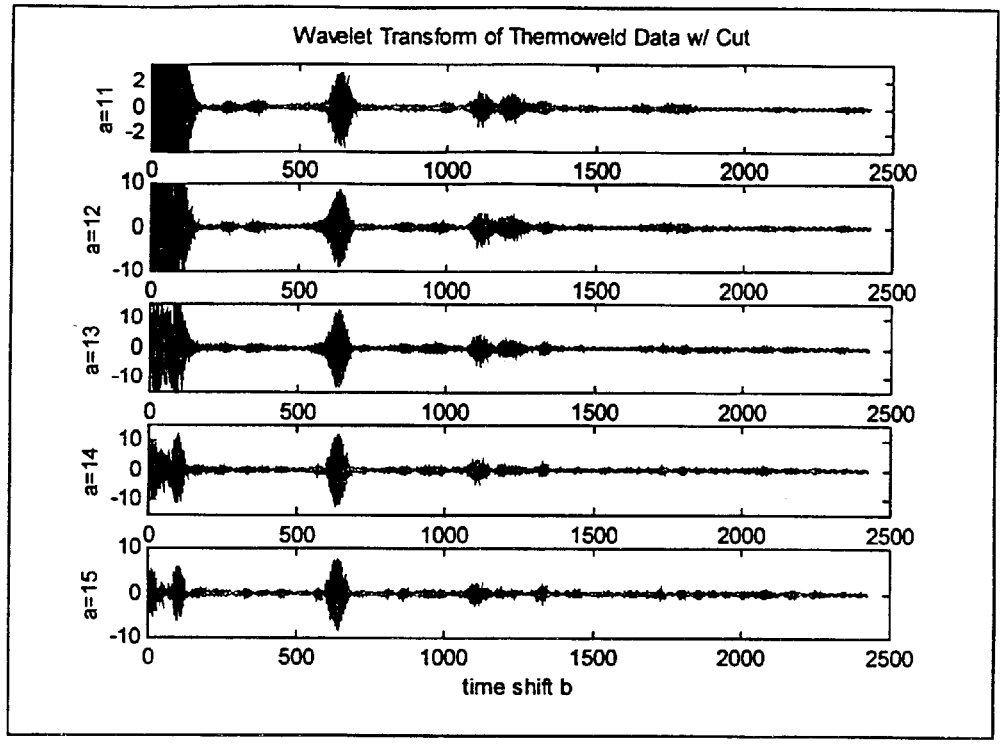
FIG. 6 illustrates a wavelet transform for a conductor flaw processed in accordance with an embodiment of the invention.

This wavelet is used for the wavelet transform. The integral wavelet transform is $$(W_\psi f)(b, a) = |a|^{-1/2} \int_{-\infty}^{\infty} f(x)\psi\left(\frac{x-b}{a}\right)dx \quad \text{(Chui 1992)}$$

where b is the time shift in this case and a is the dilation or scale. Notice the similarity to the Fourier transform. The coefficients for the transform are calculated across all time (all b) and for scales of interest (vector of a's). The result of this transform on one data set is shown in FIG. 6. Notice that the amplitude of the third wave packet in time for each scale decreases relative to the amplitude of the other wave packets. This suggests that the third packet contains a narrower bandwidth.

There are several features that are extracted from this image of the wavelet transform coefficients. These features include the time, the amplitude, the area, the frequency of greatest amplitude, and other characteristics of the wave packets. In order to find these features in the image, a robust peak detector is required.

To define the wave packets as a whole, the envelope or outline of the oscillations is required. A median filter is chosen to create an envelope of the data. Median filtering has an advantage over mean filtering in that the smearing of features by a median filter is much less than that of a mean filter. In other words, sharp details are preserved much better. This results in an outline of the wave packets which is close to what would be drawn manually. The median filtering is accomplished by simply taking the median of a window of the data and advancing that window over time.

Peak detection is performed on the envelope of the data. A simple peak detector is not sufficient for this application because it will find every peak in the data. The only peaks of interest to find a wave packet are those which have a considerably greater amplitude than the noise. These peaks are found by taking the forward difference of the envelope and looking for threshold values in the forward difference. The forward difference is $$\frac{dy(i)}{dt} = y(i+l) - y(i)$$

where y is the envelope vector in this case. Also, non-maximal suppression is performed on the peaks to remove undesirable peaks which may still be present. This is accomplished by looking forward and backward in time around each peak. The algorithm checks peaks which may have greater amplitude ahead of and behind the peak of interest in time until either the magnitude of the envelope falls below a threshold or a detector on one scale of the wavelet transform envelope.

Figure 7:
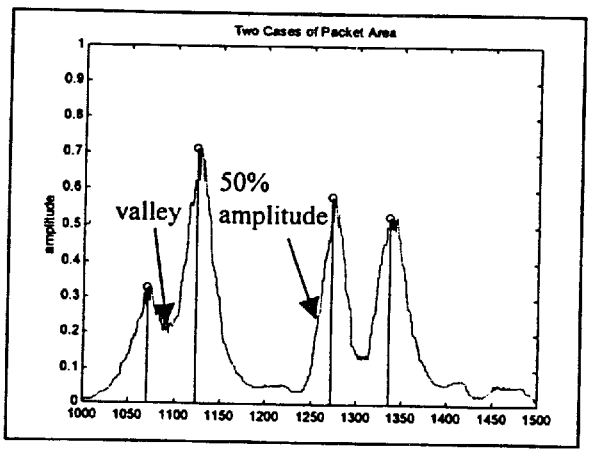
FIG. 7 illustrates packet data processed in accordance with an embodiment of the invention.

Once the peaks of the wave packets are found, these peaks are used to find the area under the envelope curve for each packet now defined by a peak. The area of each wave packet is found in two parts. The lower portion of the area is calculated by summing the envelope curve (median filtered data) from the point before the peak where the curve falls below 50% of the peak amplitude or where a valley is found between two peaks up to the peak. Similarly, the upper portion of the area is calculated by summing the envelope curve from the point just past the peak to either a valley between peaks or where the curve falls below 50% of the amplitude of the peak of interest. FIG. 7 shows both cases where a valley defines the packet and where 50% peak amplitude defines the packet. This measure is useful when compared to the peak amplitude.

Figure 8:
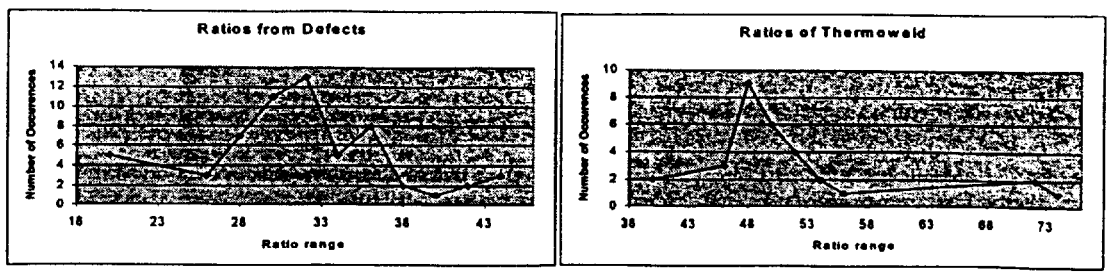
FIG. 8 illustrates packet ratio distributions processed in accordance with an embodiment of the invention.

A ratio of the packet area divided by the packet peak amplitude gives some indication of a type of conductor flaw called a thermoweld joint. This ratio does not change with time because it is a measure of the shape of the wave packet and not the size. The average ratio of packets found in the wavelet transform of the data from test specimens with a thermoweld joint indicate that the ratio increases when a reflection from a thermoweld joint is present. The average ratio for reflections that are known to result from the loose ends of a specimen or from a defect (cut) is 33.46, as shown in FIG. 8. This compares to the average ratio of a reflection from a thermoweld of 49.13.

The classification module 58 processes the data from the wavelet analyzer 55. The classification module may include a fuzzy logic module 62 to implement a fuzzy logic rule base. For example, the ratio of the peak amplitude of a wave packet to its area gives a strong indication of a thermoweld joint in a ground mat riser. This ratio becomes higher when a reflection from a thermoweld is present. In addition, the frequency content, or the scale of highest amplitude response, is different for two out of three thermoweld experiments. Based upon this limited sampling, it is likely that a reflection from an appropriate connection of a ground mat may be classified.

Assuming that the reflection from the end connections of a riser can be found, several rules may be defined to indicate the existence of defects in a riser. First, the initial wave packet indicates that the sensor is actively working. This packet is ignored in the decision making process. If there is a reflection having a relatively low amplitude to area ratio with maximum amplitude in a scale similar to the initial packet, then a defect is likely present. if one or more wave packets are received with relatively high amplitude to area ratio, then a defect is most likely not present. This type of rule classification lends itself to implementation using fuzzy rules. The fuzzy logic module 62 is used for this purpose.

A neural network module 60 may also be used to characterize the wavelet data. In one embodiment, the neural network module 60 is trained to identify wavelet patterns corresponding to wavelet patterns stored in the feature profiles 56. Once a measured wavelet pattern is matched to a wavelet pattern stored in the feature profile 56, the characteristics of the conductor flaw can be defined. For example, the type and location of the flaw can be specified based upon the parameters associated with the selected feature profile 56.

Figure 9:
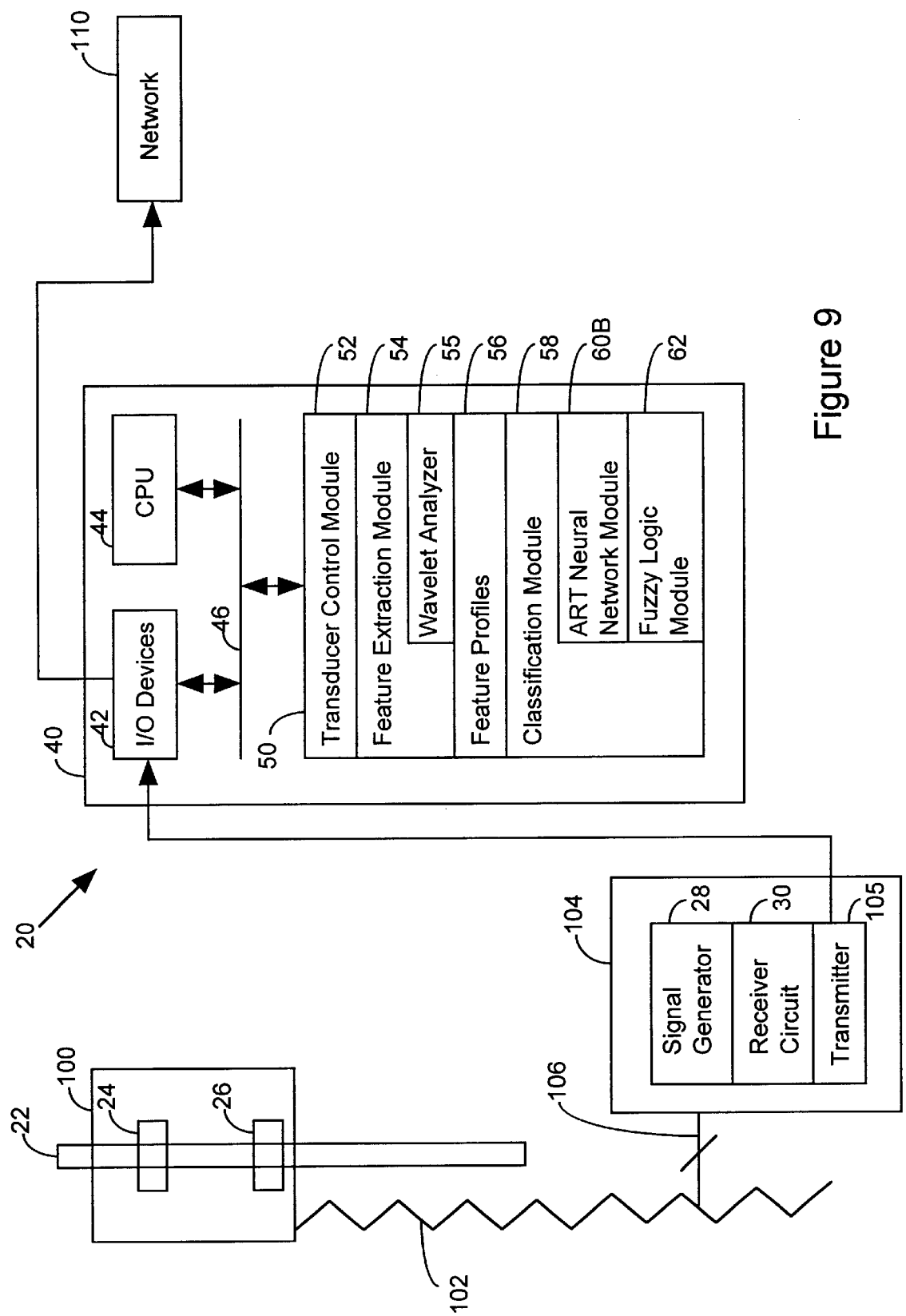
FIG. 9 illustrates an alternate embodiment of the system of FIG. 1.

FIG. 9 illustrates an alternate embodiment of the invention. FIG. 9 illustrates that the transmitting electro-magnetic acoustic transducer 24 and the receiving electro-magnetic acoustic transducer 26 share a common housing 100. The common housing 100 makes it easier to attach the transducers to the conductor. A positioning mechanism 102 may be used to position the housing at a desired location, such as a transmission line.

In the embodiment of FIG. 9, the signal generator 28 and the receiver circuit 30 are positioned in a single housing 104. A bus 106 extends along the positioning mechanism 102 to the transducers 24 and 26 to route signals. A wireless transmitter 105 may be used to send signals to a remotely positioned processing unit 40. Alternately, the processing unit 40 may be positioned within the housing 104.

A wireless transmitter may also be incorporated into the input/output devices 42 of the processing unit 40. This transmitter may then be used for remote communication with a network 110. The network 110 can be used to route the accumulated information to various utilities, where the information can be displayed.

FIG. 9 also illustrates an Adaptive Resonant Theory (ART) neural network module 60B, which may be used for signature analysis. The ART neural network module 60B is an unsupervised learning network with a large degree of robustness, which is well suited for signature analysis and diagnostic systems.

The foregoing description, for purposes of explanation, used specific nomenclature to provide a thorough understanding of the invention. However, it will be apparent to one skilled in the art that the specific details are not required in order to practice the invention. In other instances, well known circuits and devices are shown in block diagram form in order to avoid unnecessary distraction from the underlying invention. Thus, the foregoing descriptions of specific embodiments of the present invention are presented for purposes of illustration and description. They are not intended to be exhaustive or to limit the invention to the precise forms disclosed, obviously many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents.

What is claimed is:

1. An apparatus for identifying damage to an in-service conductor associated with the delivery of electric power, comprising:

a transmitting electro-magnetic acoustic transducer configured for engagement with said in-service conductor, said transmitting electro-magnetic acoustic transducer applying a transmitted signal to said in-service conductor;

a receiving electro-magnetic acoustic transducer configured for engagement with said conductor, said receiving electro-magnetic acoustic transducer acquiring a return signal from said in-service conductor that corresponds to said transmitted signal; and a feature extraction module to identify selected attributes of said return signal.

2. The apparatus of claim 1 wherein said transmitting electro-magnetic acoustic transducer generates acoustic signals with a predetermined frequency, shape, and amplitude.

3. The apparatus of claim 1 further comprising a classification module to classify selected attributes of said return signal and thereby identify damage to said in-service conductor.

4. The apparatus of claim 3 wherein said classification module classifies said selected attributes of said return signal with respect to a predetermined set of feature profiles, each feature profile characterizing a signal associated with a predetermined fault at a selected location of said in-service conductor.

5. The apparatus of claim 3 wherein said classification module includes a neural network module to classify said selected attributes of said return signal and thereby identify damage to said in-service conductor.

6. The apparatus of claim 3 wherein said classification module includes a fuzzy logic module to classify said selected attributes of said return signal and thereby identify damage to said in-service conductor.

7. The apparatus of claim 3 wherein said classification module includes a combined neural network and fuzzy logic module to classify said selected attributes of said return signal and thereby identify damage to said in-service conductor.

8. The apparatus of claim 3 wherein said classification module includes a combined Adaptive Resonant Theory neural network and fuzzy logic module to classify said selected attributes of said return signal and thereby identify damage to said in-service conductor.

9. The apparatus of claim 1 wherein said transmitting electro-magnetic acoustic transducer includes a set of magnets configured to define an axial aperture.

10. The apparatus of claim 9 wherein said transmitting electro-magnetic acoustic transducer includes a coil positioned between said set of magnets and said axial aperture.

11. The apparatus of claim 10 wherein said set of magnets includes a hinge to facilitate the re-positioning of a portion of said magnets, thereby allowing the positioning of said set of magnets around said in-service conductor, such that said in-service conductor is positioned within said axial aperture defined by said set of magnets.

12. The apparatus of claim 1 further comprising a display unit to view said return signal.

13. The apparatus of claim 1 wherein said transmitting electro-magnetic acoustic transducer and said receiving electro-magnetic acoustic transducer are positioned in a common housing.

14. The apparatus of claim 13 further comprising a positioning mechanism to selectively position said common housing at a desired location on said in-service conductor.

15. The apparatus of claim 1 wherein said return signal is routed through a wireless transmitter to said feature extraction module.

16. The apparatus of claim 1 wherein said feature extraction module is connected to a display module.

17. A method of identifying damage to an in-service conductor associated with the delivery of electric power, comprising the steps of:

generating electro-magnetic acoustic energy in an in-service conductor associated with the delivery of electric power;

measuring return electro-magnetic acoustic energy in said in-service conductor; and extracting features within said return electro-magnetic acoustic energy that characterize damage to said in-service conductor.

18. The method of claim 17 wherein said extracting step includes the step of extracting selected wavelets characterizing said return electro-magnetic acoustic energy.

19. The method of claim 18 wherein said extracting step includes the step of classifying said selected wavelets to identify damage to said in-service conductor.

20. The method of claim 19 wherein said extracting step includes the step of classifying said selected wavelets with respect to a predetermined set of feature profiles, each feature profile characterizing a signal associated with a predetermined fault at a selected location of said in-service conductor.

21. The method of claim 19 wherein said extracting step includes the step of classifying said selected wavelets through a neural network to identify damage to said in-service conductor.

22. The method of claim 19 wherein said extracting step includes the step of classifying said selected wavelets through fuzzy logic to identify damage to said in-service conductor.

23. The method of claim 17 wherein said generating step includes the step of positioning an electro-magnetic acoustic transducer around said in-service conductor.

24. The method of claim 23 wherein said generating step includes the step of positioning an electro-magnetic acoustic transducer around said in-service conductor in the form of a twisted bundle of conductors.

25. The method of claim 17 wherein said measuring step includes the step of positioning an electro-magnetic acoustic transducer around said in-service conductor.

26. The method of claim 17 further comprising the step of displaying said return electro-magnetic acoustic energy.

* * * * *